(12) United States Patent
Reinhardt (10) Patent No.: US 7,322,951 B2
(45) Date of Patent: Jan. 29, 2008

(54) ORTHOSIS FOR CORRECTING THE POSITION OF A BODY JOINT

(75) Inventor: Holger Reinhardt, Kempen (DE)

(73) Assignee: Bauerfeind AG (DE)

( * ) Notice: Subject to any disclaimer, the term of this patent is extended or adjusted under 35 U.S.C. 154(b) by 321 days.

(21) Appl. No.: 11/063,863

(22) Filed: Feb. 23, 2005

(65) Prior Publication Data

US 2005/0187506 A1 Aug. 25, 2005

(30) Foreign Application Priority Data

Feb. 24, 2004 (DE) ...................... 10 2004 008 909

(51) Int. Cl.
*A61F 5/00* (2006.01)
(52) U.S. Cl. .............. 602/16; 602/5; 602/23; 602/30
(58) Field of Classification Search ............ 602/5, 602/16, 19, 20, 21, 23–26, 30
See application file for complete search history.

(56) References Cited

U.S. PATENT DOCUMENTS

| 1,183,062 | A | * | 5/1916 | Ford ........................ 602/30 |
| 4,088,129 | A | | 5/1978 | DiGiulio |
| 4,256,097 | A | * | 3/1981 | Willis ....................... 602/16 |
| 4,353,361 | A | * | 10/1982 | Foster ....................... 602/16 |
| 5,244,455 | A | * | 9/1993 | Swicegood et al. ........... 602/16 |
| 5,658,243 | A | * | 8/1997 | Miller et al. ................ 602/26 |
| 6,059,743 | A | | 5/2000 | Reinhardt et al. |
| 6,090,057 | A | | 7/2000 | Collins et al. |
| 6,254,559 | B1 | * | 7/2001 | Tyrrell ....................... 602/16 |
| 6,488,644 | B1 | | 12/2002 | Ostrom et al. |
| 6,993,808 | B1 | * | 2/2006 | Bennett et al. .............. 16/334 |
| 2003/0109818 | A1 | | 6/2003 | Evans et al. |
| 2006/0155233 | A1 | * | 7/2006 | Huber et al. ................ 602/30 |

FOREIGN PATENT DOCUMENTS

| DE | 27 50 755 | 9/1978 |
| DE | 203 12 159 U 1 | 11/2003 |
| EP | 0 879 032 | 4/1998 |
| WO | WO 01/45600 A 1 | 6/2001 |

* cited by examiner

*Primary Examiner*—Justine R. Yu
*Assistant Examiner*—Kristen C. Matter
(74) *Attorney, Agent, or Firm*—Banner & Witcoff, Ltd.

(57) ABSTRACT

An orthosis for correcting the position of a body joint, the orthosis extending over the two members connected by the body joint and being provided with two arms forming the orthosis, the arms each being held on the respective member by a cuff and being interconnected by a pivot joint adjacent to the body joint is described. For the bending required during normal movement, the pivot joint is formed by an axle ring embraced by the one arm, and the axle ring being fixedly connected to a ring bearing eccentric with respect to the axle ring to form a central adjusting ring. The ring bearing forms a pivot bearing for the other arm and the pivot bearing being embraced by said other arm, such that the rotation plane of said ring bearing with respect to the rotation plane of the axle ring is pivotable through rotation of the adjusting ring.

10 Claims, 4 Drawing Sheets

ORTHOSIS FOR CORRECTING THE POSITION OF A BODY JOINT

The invention relates to an orthosis for correcting the position of a body joint, said orthosis extending over the two members connected by the body joint and being provided with two arms forming the orthosis, said arms each being held on the respective member by an attachment means and being interconnected by a pivot joint adjacent to the body joint.

Such an orthosis for the knee joint is described and presented in European patent specification EP 0 879 032 B1, in which the two arms of the orthosis are formed by a two-part rail comprising a pivot hinge which is offset rearwards in relation to the knee joint to adapt to the pattern of movement of the latter, and which includes a pin. The pin, since it is mounted eccentrically in a pivot bearing, connects both rail parts in a rotationally movable manner and, through the rotation of the pivot bearing, displaces the pin of the pivot hinge, this displacement providing the pin with a position which is extensively adapted to the pattern of movement of the knee joint.

Furthermore, an orthosis for correcting the position of the big toe is known from German utility model specification DE 203 12 159 U1. The orthosis serves, with an articulated bending rail extending from the metatarsus to the big toe on the inside of the foot, to provide the big toe with an orientation determined by the articulated bending rail in order thereby to remedy a defective position of the big toe consisting in an inclined position of the big toe with respect to the longitudinal direction of the foot. As an especially advantageous embodiment thereof, reference is made on page 9, last paragraph, of the publication to a carbon-fibre-reinforced plate for the articulated bending rail which is formable under the influence of heat and which, after cooling down, has a great elastic force. The material of the articulated bending rail exerts a force which corrects the position of the big toe, wherein the mobility of the big toe in the natural flexion-extension direction, i.e. the bending of the big toe during the rolling motion of the foot, is not restricted owing to the fact that the known orthosis has a joint which is rotatable about a pin, said joint allowing the said bending and extension. The customized adaptation of the articulated bending rail, which is made possible by thermally changing the orientation of the articulated bending rail, requires a considerable effort, because, as stated above, this requires the heating of the material of the articulated bending rail, which, owing to the therefor required temperatures, cannot be carried out on the patient him/herself by the specialist. It is necessary, therefore, to adapt the articulated bending rail as it were, on a trial and error basis, where necessary by repeatedly heating the articulated bending rail and each time adjusting the degree of bending. It is necessary each time for the articulated bending rail to be fitted to and removed from the patient. Should it become necessary in the course of time for the articulated bending rail to be readjusted, the patient must once again visit the specialist who has the necessary means for suitably adjusting the degree of bending of the articulated bending rail. Since it is impossible to make this adjustment on the patient's foot, it can virtually only be carried out on the basis of visual judgment, this, above all, complicating any later readjustment of the articulated bending rail as it is not possible to take account of previous initial values, because these are normally not in any way known.

The object of the invention, therefore, is to create an orthosis for correcting the position of a body joint, wherein, while maintaining the normal bending mobility of the joint, said orthosis selectively allows the desired adjustment, identified as necessary, of the plane of bending motion which can thereafter readily be readjusted on the patient.

The object of the invention is achieved by an orthosis of the type initially described and being of such design that, for the bending required during normal movement, the pivot joint is formed by an axle ring embraced by the one arm, said axle ring being fixedly connected to a ring bearing eccentric with respect to the axle ring to form a central adjusting ring, said ring bearing forming a pivot bearing for the other arm, said pivot bearing being embraced by said other arm, wherein the rotation plane of said ring bearing with respect to the rotation plane of the axle ring is pivotable through rotation of the adjusting ring by such an angle that the arm supported by the axle ring—and, with it, the thereby held member—assume a pivot position of said member in relation to the extended normal position, depending on the rotation angle of the adjusting ring with respect to the arm connected to the ring bearing.

As a result of this design, the movement of the one arm to allow bending is augmented to include the pivoting of said arm, said pivoting being steplessly adjustable over that range which is required for treating the defective position of a member of the body joint. For said adjustment it is necessary merely to rotate the ring bearing supporting the respective arm, wherein, as the ring bearing rotates and because of its eccentricity with respect to the axle ring, the ring bearing changes its rotation plane in relation to the rotation plane of the axle ring (bending movement plane) and assumes a respectively desired angle which then results in a corresponding pivot position of the arm acting on the member in question, the bending movement plane of which is thus correspondingly pivoted. Consequently, decisive importance is attached to the design-based combination of these two required rotations in the central adjusting ring, embracing the ring bearing fixedly connected to the axle ring, because the adjusting ring acts, similarly to a universal joint, over the angular range required in this connection for the pivot position of the respective member, albeit without the need for a second axle, the fixed connection between axle ring and ring bearing resulting in an especially compact design in the lateral direction, this allowing the orthosis to be worn without discomfort.

The orthosis according to the invention may be used in connection with all body joints which are required to execute a bending movement in which the bending movement plane may need to be adjusted with regard to its angle in relation to the normal bending movement plane. This is necessary, for example, for correcting the position of the big toe or for correcting the position of the knee joint, but is, of course, likewise possible on other body joints.

An orthosis for correcting the position of the big toe with two arms extending from the metatarsus to the big toe on the inside of the foot and being secured to the metatarsus and to the big toe by respective cuffs is advantageously of such design that, for the bending required during rolling of the foot, the pivot joint is formed by the axle icing embraced by the one arm, and the ring bearing embraced by the other arm determines a pivot position of the former arm in relation to the extended normal position, depending on the rotation angle of the adjusting ring.

Through rotation of the adjusting ring it is then possible to adjust the bending movement plane within the range required for correcting the position of the big toe and thus suitably to correct the defective position of the big toe, it being especially advantageous that such adjustment can be performed with the orthosis fitted on the patient.

A further example of the application of the orthosis according to the invention is the correction of the position of the knee joint by means of two arms of the orthosis, said two arms extending from the thigh through the knee joint to the lower leg, being secured to the thigh and lower leg by respective cuffs and being interconnected by a pivot joint adjacent to the knee joint. Said orthosis is advantageously of such design that, for the bending required during movement of the knee joint, the pivot joint is formed by the axle ring embraced by the one arm, and the ring bearing embraced by the other arm determines a pivot position of the former arm in relation to the extended normal position, depending on the rotation angle of the adjusting ring.

Through the respective adjustment of the adjusting ring it is possible to adjust the orthosis to counteract both knock-knees and also bow-legs, this once again being possible with the orthosis fitted on the patient.

In order to make it clearly apparent both to the patient and to the attending physician what is the present pivot position of the arm acting on the big toe, the arm embracing the axle ring may be provided with an annular scale, said annular scale indicating the rotation angle of the ring bearing and therefore the pivot position of the arm which is in contact with the big toe. The rotation of the ring bearing—during which rotation the axle ring slidingly rotates in the arm embracing it—can easily be effected using any tool which in any manner engages the ring bearing. An example of this will be given hereinbelow.

In order to accomplish a secure connection between the two arms and the adjusting ring, it is possible advantageously to employ an expanding ring pressed into the axle ring, wherein, by expanding in the direction of the axle ring or ring bearing, said expanding ring ensures that the connection of the aforementioned parts cannot become undone as long as the expanding ring is pressed in. Said expanding ring can also be used to engage recesses in the ring bearing with its edge, as is the case in known manner in electronic devices by means of a coin. The expanding ring is used to adjust the respectively desired rotation angle of the ring bearing, this then adjusting the necessary pivot position of the arm which is in contact with the big toe. Thereafter the expanding ring is then pressed into the axle ring, thereby securing the entire connection.

In order to permit the effective use of the orthosis with its aligning effect on the big toe also in those cases in which, for medical reasons, there must be no rolling of the foot, e.g. after a preceding operation, the big toe thus needing to be kept in straight alignment without being able to carry out any bending, it is advantageous for the arm embracing the axle ring to be provided with a selectively attachable anti-rotation means which locks together the arm and the axle ring in such a manner that the arm is no longer able to rotate about the axle ring. This may be accomplished, for example, by any form of selectively engageable toothing. This ensures that, while maintaining the desired pivot position of the arm which is in contact with the big toe, said arm is unable to rotate about its axle ring, i.e. the big toe is securely kept in its adjusted position, this being the case for as long as the anti-rotation means is fitted.

In order to design the orthosis such that it can be worn without any unpleasant pressure being exerted, the arms may be provided on their side facing the member with suitable pads.

It is advantageous for the axle ring and the ring bearing to be integral with each other and, in particular, for them to be formed from a plastic moulding which is easy to manufacture and which also possesses the requisite strength and elasticity for securing purposes.

An illustrative embodiment of the invention is presented in the drawings, in which:

FIG. 4a, b, c show the joint of the orthosis in section, with the adjusting ring adjusted to correct the big toe of a right foot with the big toe displaced to the left;

FIG. 5a, b, c show the same joint in cross section, with the adjusting ring rotated such that the position of the big toe of a right foot is kept normal;

FIG. 6a, b, c show the same joint, with the adjusting ring adjusted for a right foot with the big toe displaced to the right;

Figure 1:
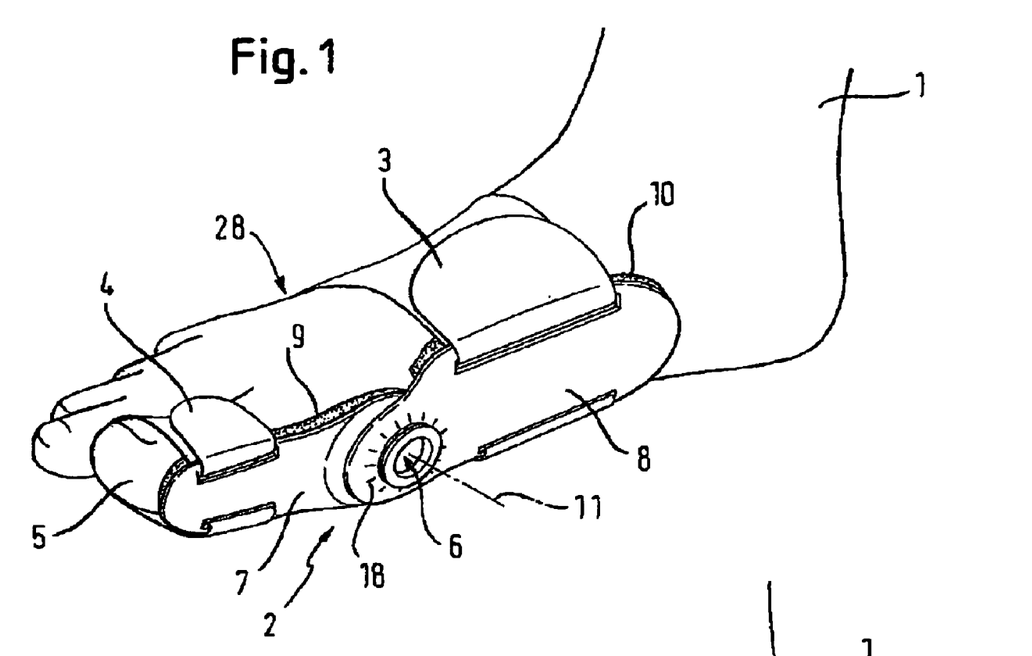
FIG. 1 shows the orthosis fitted to a right foot.

FIG. 1 shows the orthosis 2 fitted to a right foot 1 and in a position in which the orthosis 2 is fitted to the metatarsus 28 by the securable bandage 3 and to the big toe 5 by the likewise securable bandage 4 with the foot in the normal position. The orthosis 2 is provided approximately at its centre with the joint 6 which divides the orthosis 2 into the toe arm 7 and the metatarsus arm 8. Both the toe arm 7 and also the metatarsus arm 8 are provided on their side facing the foot with respective pads 9 and 10 which ensure that the orthosis 2 can be worn without discomfort. The two bandages 3 and 4 are of known design, the bandage 3 supporting the metatarsus arm 8 and the bandage 4 supporting the toe arm 7.

Figure 2:
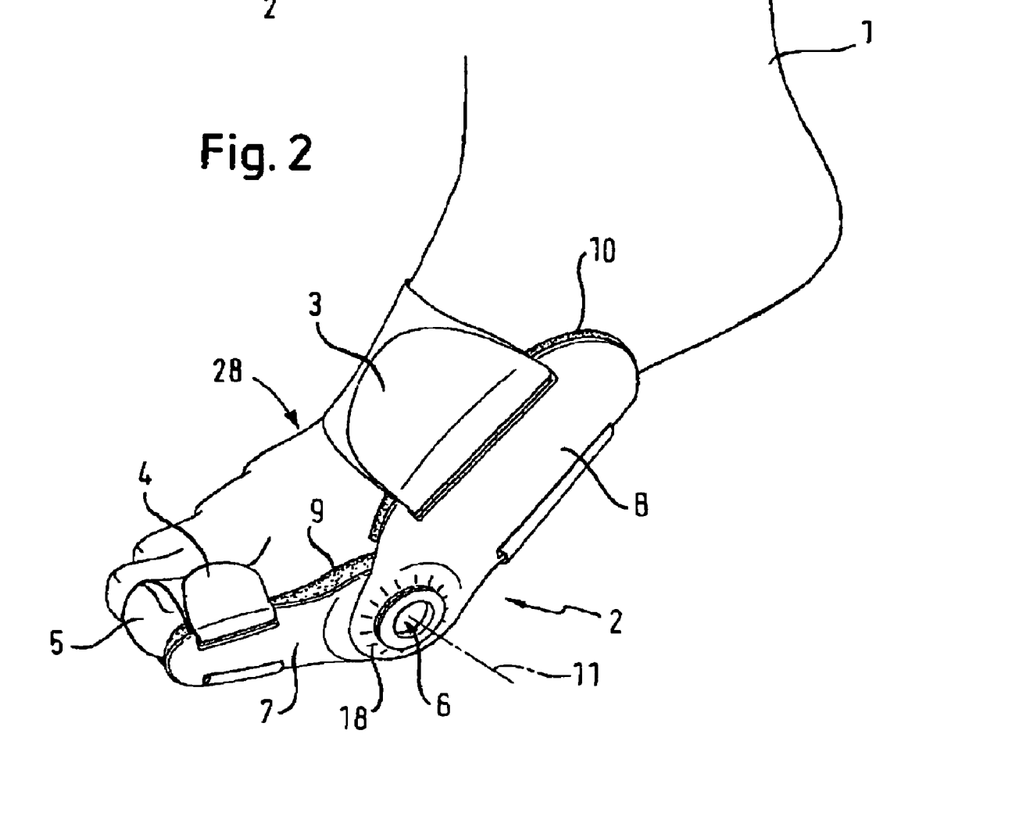
FIG. 2 shows the same orthosis with toes bent.

The joint 6 allows the orthosis 2, during rolling of the foot 1, as shown in FIG. 2, to bend the toes and therefore the big toe 5 in relation to the metatarsus 28. For this purpose, the joint 6 has a rotatable design, which will be referred to in greater detail in connection with FIG. 4 to 6. The effect of a pivot bearing is represented in FIGS. 1 and 2 by the dash-dotted line 11 drawn on the joint 6.

Figures 4A, 4B, 4C:
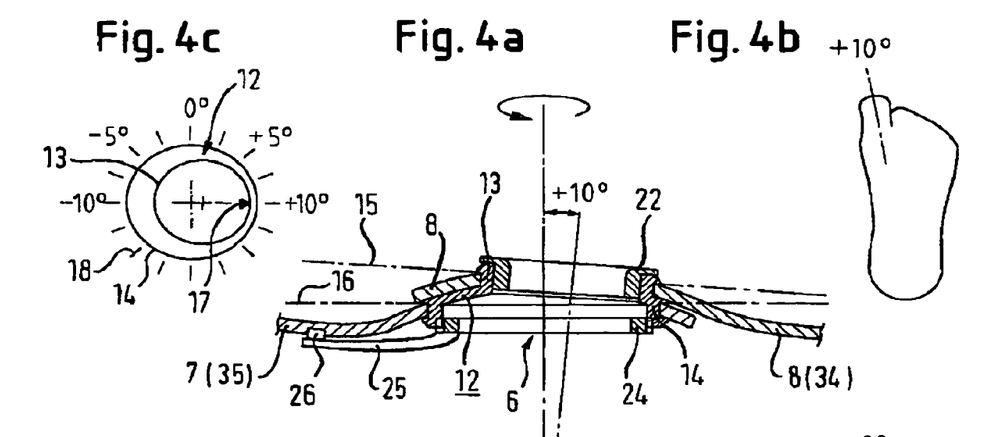
Figures 5A, 5B, 5C, 6A, 6B, 6C:
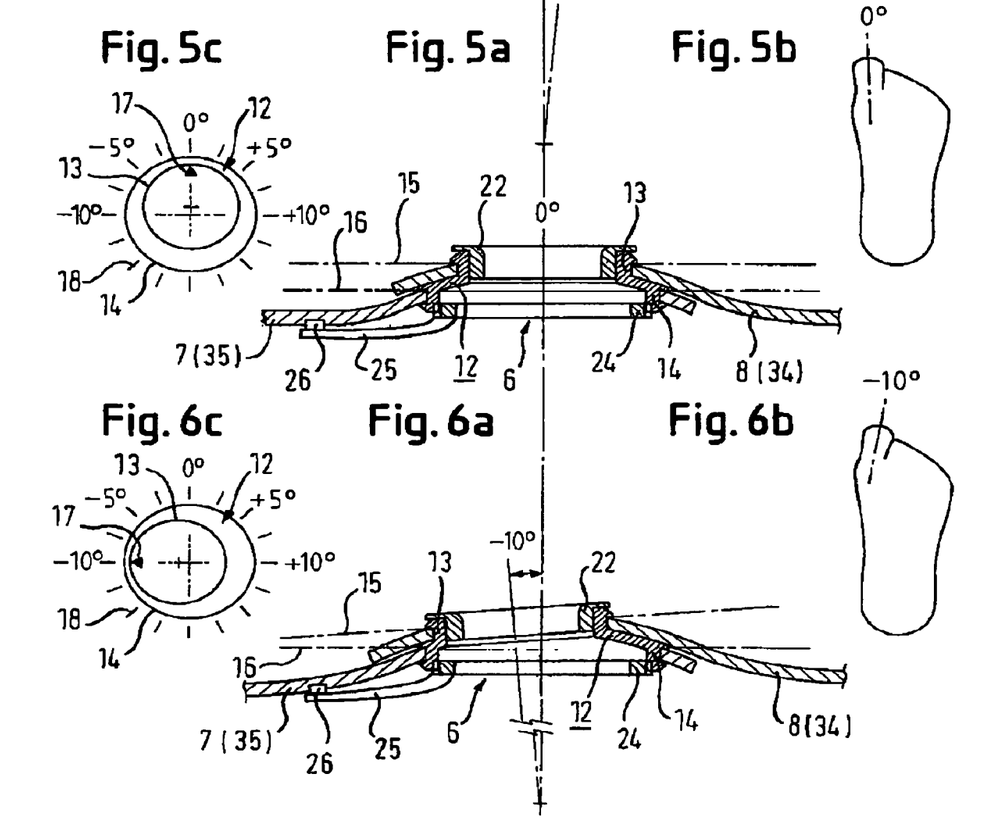

The design of the joint 6 according to FIGS. 1 and 2 is presented in greater detail in FIG. 4 to 6, various settings of the joint 6 being shown. The joint 6 contains an adjusting ring 12 in which the ring bearing 13 for the metatarsus arm 8 is united with the axle ring 14 for the toe arm 7. For this purpose, the adjusting ring 12 is integrally joined to the axle ring 14 and the ring bearing 13.

Figure 3:
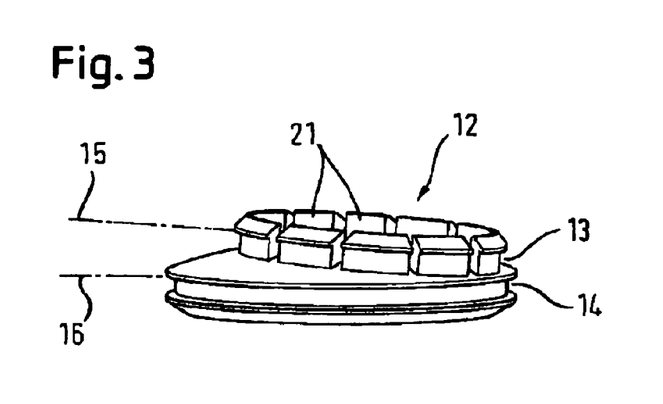
FIG. 3 shows the adjusting ring responsible for the position of the big toe.

In order to illustrate the design and operating principle of the adjusting ring 12, reference is made to FIG. 3, which clearly shows the particular design of the adjusting ring 12, above all with regard to the inclined position of the rotation plane 15 of the ring bearing 13 in relation to the rotation plane 16 of the axle ring 14. When the adjusting ring 12 is rotated, the portion with the ring bearing 13 travels, as it were, around the centre of the adjusting ring 12 according to its eccentricity, moving—owing to the changing position of the rotation plane 15—from one extreme relative position (see FIG. 4a) to the other extreme relative position (see FIG. 6a).

The attachment of the metatarsus arm 8 and of the toe arm 7 in the respective portions of the adjusting ring 12, i.e. in the axle ring 14 and the ring bearing 13, is accomplished, as is clearly shown in FIGS. 4a, 5a and 6a, through the engagement by respective edges of the axle ring 14 and of the ring bearing 13 of the corresponding circular recesses in the metatarsus arm 8 and in the toe arm 7 (see also FIG. 7), with the result that both the toe arm 7 and also the metatarsus arm 8 are able to be rotated in relation to the adjusting ring 12. The uniting of toe arm 7 and metatarsus arm 8 in the adjusting ring 12 is accomplished in that the respective arms are latched onto the corresponding attachment components, i.e. axle ring 14 and ring bearing 13, it being the case that, owing to a corresponding elasticity of the adjusting ring 12, there is a backing-off of the respective engaging edge, for which purpose said engaging edge is provided with an externally starting bevel form, as a consequence of which, therefore, the two arms 7 and 8 can be connected together to the adjusting ring 12 such that the adjusting ring 12 tightly holds the two arms 7 and 8, which, however, can still be rotated with respect to the adjusting ring 12.

The adjusting ring 12 can be selectively adjusted in relation to the metatarsus arm 8 through rotation of the ring bearing 13, wherein, owing to the eccentricity of the ring bearing 13 with respect to the axles ring 14 and owing to the inclination of the rotation plane 15 of the ring bearing 13 with respect to the rotation plane 16 of the axle ring 14, there is a respective pivot angle of the toe arm 7, as is presented in the sequence of FIGS. 4a, 5a and 6a, from +10° to an angle of −10° for the attachment of the toe arm 7, which is thereby moved from a deflected position pointing away from the foot (presented in FIG. 4b) through its normal position (shown in FIG. 5b) into a deflected position pointing inwardly to the foot (presented in FIG. 6b). This ensuing displacement of the rotation plane 15 results in the above-discussed adjustment of the toe arm 7, which, owing to its fixed contact with the big toe 5, pivots the big toe 5 into a corresponding position.

Consequently, through rotation of the adjusting ring 12, the attachment of the toe arm 7 respectively determines the position of the big toe as presented in connection with FIGS. 4b, 5b and 6b, wherein the rotation inside the joint during bending of the toes (see FIG. 2) takes place in the region of the connection between axle ring 14 and toe arm 7. During said rotation owing to the aforementioned bending, therefore, the attachment of the metatarsus arm 8 in the ring bearing 13 remains unchanged, with the consequence that, irrespective of the degree of bending, the adjustment of the toe arm 7 according to the previously made adjustment of adjusting ring 12 with respect to the metatarsus arm 8 is maintained.

FIGS. 4c, 5c and 6c schematically present the respective adjustments of the adjusting ring 12 with respect to the metatarsus arm 8, the inner circle symbolizing the ring bearing 13 and the outer circle symbolizing the axle ring 14. Indicated on the metatarsus arm 8 around the adjusting ring 12 is a scale 18 with degrees of angle, as also shown in principle in FIGS. 1 and 2. Provided opposite said scale 18 on the ring bearing 13 is a mark 17 which, with reference to a corresponding value on the scale 18, indicates the present degree of pivot of the toe arm 7 with respect to the normal position (0°), the toe arm 7 being correspondingly pivoted (sec the respective degrees of angle indicated in FIGS. 4b, 5b and 6b) and then maintaining such adjustment irrespective of whether bending of the toes results in the rotation of the adjusting ring 12 in relation to the toe arm 7, such rotation taking place in the region of the axle ring 14.

Figure 7:
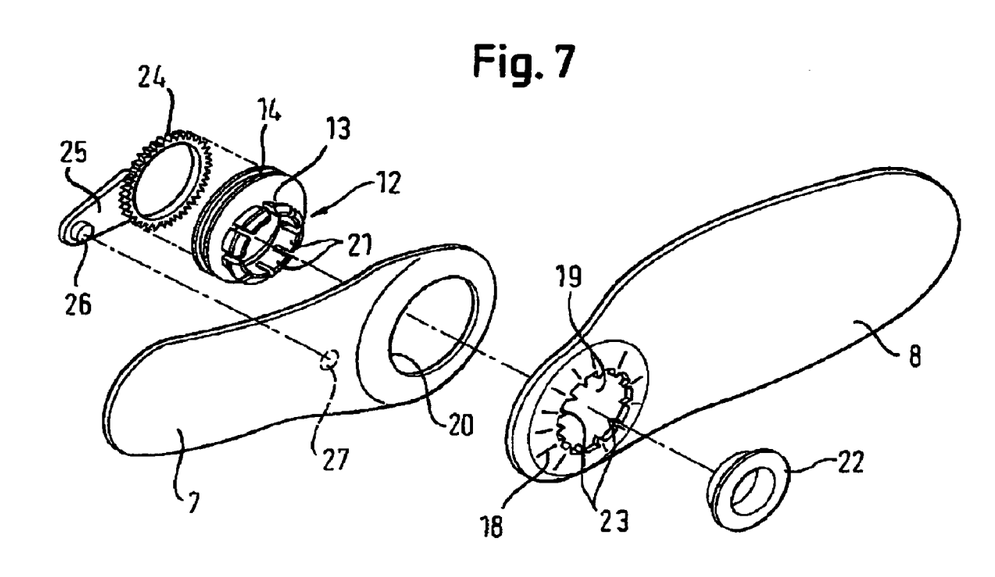
FIG. 7 shows an exploded view of the principal components of the joint as presented in FIG. 4 to 6.

FIG. 7 presents an exploded view of the construction of the joint 6, showing next to each other the metatarsus arm 8 and the toe arm 7, which are held together with their aligning recesses 19 and 20. This is accomplished by the adjusting ring 12, which consists of the ring bearing 13 and the axle ring 14. During the assembling of adjusting ring 12, toe arm 7 and metatarsus arm 8, the ring bearing 13 penetrates the recesses 20 and 19 until finally, owing to the elasticity of the individual ribs 21 of the ring bearing 13, said ring bearing 13 latches behind the respective edge of the recess 19 in the metatarsus arm 8, as a consequence of which the three aforementioned parts are connected together. Provided in order to secure such connection is the expanding ring 22, which fits into the hole in the ring bearing 13 and presses the individual ribs thereof in an outward direction. In addition, the expanding ring 22 ensures that a once adjusted angular position of the adjusting ring 12 with respect to the metatarsus arm 8 remains secured. This is accomplished in that provided in the recess 19 of the metatarsus arm 8 are projections 23 which engage the gaps between the individual ribs 21 in the ring bearing 13. Such engagement is released by removing the expanding ring 22, with the result that, with the expanding ring 22 removed, it is possible to achieve the adjustment of the adjusting ring 12 as presented in connection with FIGS. 4, 5 and 6. After an adjustment has been made, the expanding ring 22 is then inserted, as a consequence of which the adjusted degree of pivot for the toe arm 7 is maintained.

FIG. 7 presents yet a further method of securing, this time in the form of the anti-rotation means 24, which can be pressed into the recess in the axle ring 14, where it becomes firmly embedded in the recess with its teeth. Said anti-rotation means 24 ensures that, if necessary for therapeutic reasons, the toe arm 7 is prevented from bending, this possibly being required for a short period of time after an operation. For this purpose, the anti-rotation means 24 is then inserted with its extension 25 and the locking button 26 into a corresponding hole 27 in the toe arm 7, thereby fixing the position of the toe arm 7 for the period of insertion of the anti-rotation means 24 (see also FIGS. 4a, 5a, 6a).

The orthosis according to the invention, which is presented in the drawings with reference to a right foot, can, of course, also be transferred to a left foot, the orthosis in this case being fitted, as it were, in a mirror image on a left foot without there being any change to the internal construction of the orthosis. The rotation of the adjusting ring 12 shown in FIGS. 4c, 5c and 6c takes place over the top part of the scale 18 in the drawings and was thus based on a right foot. If the orthosis is fitted to a left foot, use is made of the bottom part of the scale, which is, as it were, a mirror image of the top part. Consequently, it is possible with a circumferential scale engraved in the metatarsus arm to use said scale in connection with both a right foot and also a left foot. Equally, it is possible to exchange the ring bearing, shown on the outside in the illustrative embodiment, and the axle ring, shown on the inside, with the consequence, therefore, that the axle ring would be positioned on the outside. In either case, the one arm is still associated with the axle ring and the other arm with the ring bearing, or vice versa, without there being any change to the operating principle of the joint.

FIGS. 8 and 8a to c present a further illustrative embodiment of the application of the orthosis according to the invention, this being a knee joint orthosis fitted to the thigh 30 and lower leg 31 of the leg containing the knee joint 32, for which purpose the kneecap is schematically indicated by reference character 33. The knee joint orthosis has the two arms 34 and 35, which are each secured to the thigh 30 and to the lower leg 31 by securing means in the form of cuffs 36 and 37. The cuffs are of known design. The two arms 34 and 35 are interconnected by the pivot joint 6, which, with regard to its internal design, is completely identical to the pivot joint 6 shown in FIG. 1 to 7. In particular, reference is made in this regard to FIGS. 4a, b, c, 5a, b c and 6a, b, c, the positions from which likewise occur in basic manner in FIGS. 8a, b and c. With regard to the bending movement of the knee joint 32 and the respective lateral pivoting of the knee joint 32, reference is made to the representations in FIGS. 4a, 4c, 5a, 5c, 6a, 6c.

Figure 8:
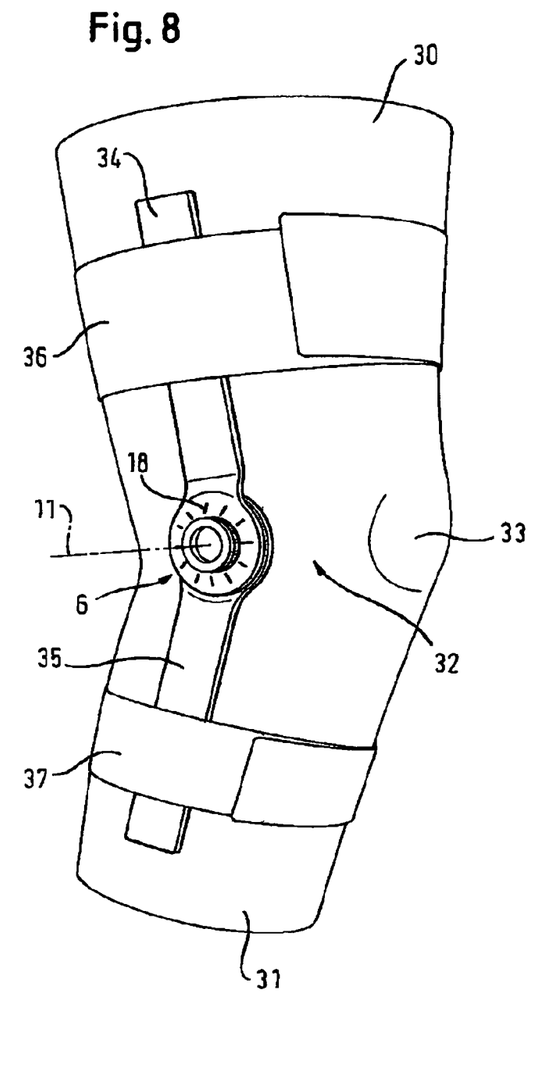
FIG. 8 shows the orthosis fitted to a leg, in a perspective view.
Figure 8A:
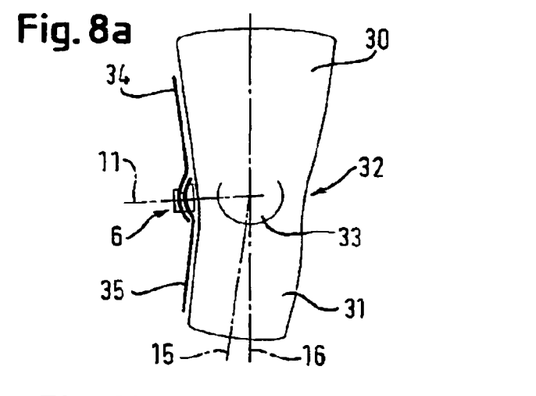
FIG. 8a, b, c show the same orthosis fitted to a leg, in a view of the knee joint, wherein, in order to simplify the representation, the cuffs for attaching the orthosis have been omitted.
Figure 8B:
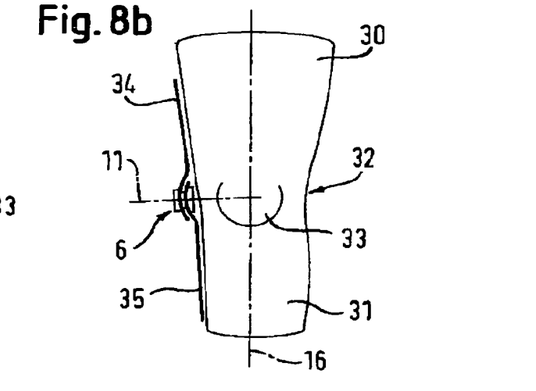
Figure 8C:
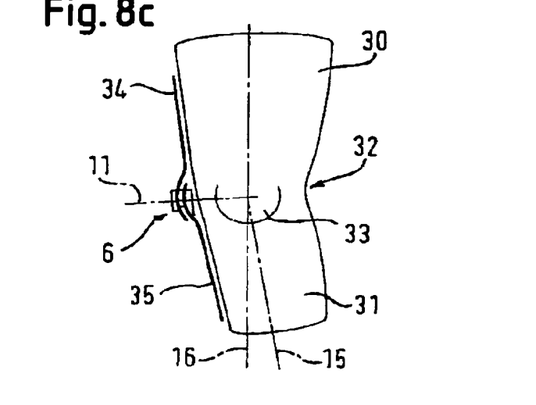

FIGS. 8a, 8b and 8c likewise present the rotation planes 15 and 16 shown in FIGS. 4a, 5a and 6a, albeit laterally offset towards the centre of the knee joint 32. The displacement of the rotation plane 16 shown in FIGS. 8a and 8c results from a corresponding rotation of the adjusting ring rotated in the pivot joint 6, this correspondingly adjusting the position of the arm 35 with respect to the arm 34, as becomes clear from a comparison of FIGS. 8a and 8c, the rotation plane 15 in the normal position as in FIG. 8b coinciding with the rotation plane 16 which is responsible for the normal bending movement of the knee joint 32.

As is described herein and for ease of reference, the orthosis may be considered as having an assembled and a disassembled configuration. The orthosis as it appears in FIGS. 1 and 2 is illustratively depicted as being in an assembled configuration. In FIGS. 1 and 2 arms (7, 8) are pivotally connected via pivot joint (6) including central adjusting ring (12) to allow certain movement relative to one another. The orthosis is configured to have other various specific arrangements, positions or configurations that are not specifically shown in figures may also be considered an assembled including a configuration in which arms (7, 8) are pivotally connected via pivot joint (6) which has central adjusting ring (12) including a assembled configuration prior but prior to be attached to a body part such as a knee, toe, foot or the like.

Also, FIG. 7 shows an illustrative depiction of the orthosis in a disassembled configuration. Similarly, FIG. 3 provides an illustrative depiction of the central adjusting ring (12). The central adjusting ring (12), including the ring bearing (13) and the axle bearing (14), is fixedly connected as a single unitary component. The ring bearing (13) and axle bearing (14) have fixed non-modifiable eccentricity relative to one another regardless of whether the orthosis is in a assembled or a disassembled configuration. Various other specific disassembled configurations are not shown but may be accomplished consistent with that shown in FIGS. 3 and 7.

With regard to use on the right or left knee joint, there applies that which was stated above in connection with the right or left foot. However, it is, of course, readily possible for the orthosis according to the invention to be fitted to the inside or outside of the knee joint, this being made possible by the low overall height of the orthosis with its pivot joint 6.

What is claimed is:

1. Orthosis (2) for correcting the position of a body joint (6), said orthosis (2) configured to extend over two members (5, 28;30,31) connected by a body joint and being provided with a first arm (7,35) and a second arm (8,34) forming the orthosis (2), said first (7,35) and second (8,34) arms each being configured to hold on the respective member (5, 28; 30, 31) by an attachment means (3, 4; 36, 37) and being interconnected by a pivot joint characterized in that, the pivot joint (6) includes a unitary central adjusting ring (12) formed by an axle ring (14) embraced by the first arm (7) and a ring bearing (13) with a fixed eccentricty with respect to the axle ring (14) and embraced by the second arm (8), wherein a variable rotation plane (15) of said ring bearing (13) is configured to be varied with respect to a fixed rotation plane (16) of the axle ring (14) by rotation of the adjusting ring (12) by such an angle that the first arm (7) supported by the axle ring (14) assumes a pivot position in relation to the extended normal position, depending on the rotation angle of the adjusting ring (12), wherein the orthosis includes an assembled and a disassembled configuration and the central adjusting ring has a fixed eccentricity in both the assembled and disassembled configuration.

2. Orthosis according to claim 1 configured for correcting the position of a big toe (5) with the first and second arms (7, 8) configures to extend from a metatarsus (28) to the big toe (5) on the inside of the foot (1), said first and second arms (7, 8) being configured to be secured to the metatarsus (28) and to the big toe (5) by respective cuffs (3, 4) and interconnected by a pivot joint (6) adjacent to big toe (5), characterized in that, for the bending required during rolling of the foot, the pivot joint (6) is formed by the axle ring (14) embraced by the first arm (7) and the ring bearing (13) embraced by the second arm (8) a determines a pivot position of the first arm (7) in relation to the extended normal position, depending on the rotation angle of the adjusting ring (12).

3. Orthosis according to claim 1 configured for correcting the position of a knee joint (32) with the first and second arms (34, 35), configured to extend from a thigh (30) through the knee joint (32) to a lower leg (31), said first and second arms (34, 35) being configured to be secured to the thigh (30) and lower leg (31) by respective cuffs (36, 37) and interconected by a pivot joint (6) adjacent to the knee joint (32), characterized in that, for the bending required during movement of the knee joint, the pivot joint (6) is formed by the axle ring (14) embraced by the first arm (35), and the ring bearing (13) embraced by the second arm (34) to determine a pivot position of the first arm (35) in relation to the extended normal position, depending on the rotation angle of the adjusting ring (12).

4. Orthosis according to claim 1 characterized in that the arm (7) embracing the axle ring (14) is provided with an annular scale (18), said annular scale (18) indicating the rotation angle of the ring bearing (13) and therefore the pivot position of the other arm (8).

5. Orthosis according to claim 1, characterized in that a connection of the first and second arms (7, 8) and the adjusting ring (12) is secured by an expanding ring (22) pressed into the axle ring.

6. Orthosis according to claim 1, characterized in that the second arm (8) embracing the axle ring (14) has a selectively attachable anti-rotation means (24).

7. Orthosis according to claim 1, characterized in that the first and second arms (7, 8) includes pads (9, 10) positioned on a side that faces the respective member (5, 28; 30, 31).

8. Orthosis according to claim 1, characterized in that the axle ring (14) and the ring bearing (13) are integral with each other.

9. Orthosis (2) for correcting the position of a body joint (6), said orthosis (2) configured to extend over two members (5, 28;30,31) connected by a body joint and being provided with a first arm (7,35) and a second arm (8,34) forming the orthosis (2), said first (7,35) and second (8,34) arms each being configured to hold on the respective member (5, 28; 30, 31) by an attachment means (3, 4; 36, 37) and being interconnected by a pivot joint characterized in that, the pivot joint (6) includes a unitary single component central adjusting ring (12) having an axle ring (14) configured to embrace the first arm (7) and a ring bearing (13) with a fixed eccentricity with respect to the axle ring (14) and configured to embrace the second arm (8), wherein a variable rotation plane (15) of said ring bearing (13) is configured to be varied with respect to a fixed rotation plane (16) of the axle ring (14) by rotation of the adjusting ring (12) by such an angle that the first arm (7) supported by the axle ring (14) assumes a pivot position in relation to the extended normal position, depending on the rotation angle of the adjusting ring (12).

10. Orthosis (2) for correcting the position of a body joint (6), said orthosis (2) configured to extend over two members (5, 28;30,31) connected by a body joint and being provided with a first arm (7, 35) and a second arm (8, 34) forming the orthosis (2), said first (7, 35) and second (8, 34) arms each being configured to hold on the respective member (5, 28; 30, 31) by an attachment means (3, 4; 36, 37) and being interconnected by a pivot joint characterized in that, the pivot joint (6) includes a central adjusting ring (12) unitarily formed by an axle ring (14) embraced by the first arm (7), and a ring bearing (13) with a fixed eccentricty with respect to the axle ring (14) and embraced by the second arm (8), wherein a variable rotation plane (15) of said ring bearing (13) is configured to be varied with respect to a fixed rotation plane (16) of the axle ring (14) by rotation of the adjusting ring (12) by such an angle that the first arm (7) supported by the axle ring (14) assumes a pivot position in relation to the extended normal position, depending on the rotation angle of the adjusting ring (12), wherein the orthosis is configured such that the position of the variable rotation plane can be modified while the orthosis is worn.

\* \* \* \* \*

UNITED STATES PATENT AND TRADEMARK OFFICE
CERTIFICATE OF CORRECTION

PATENT NO.        : 7,322,951 B2                                  Page 1 of 1
APPLICATION NO. : 11/063863
DATED             : January 29, 2008
INVENTOR(S)       : Holger Reinhardt

It is certified that error appears in the above-identified patent and that said Letters Patent is hereby corrected as shown below:

In Column 8, Claim 2, Line 22:
    Please replace "a determines" with --to determine--

In Column 10, Claim 10, Line 3:
    Please replace "the first arm (7)," with --the first arm (7)--

Signed and Sealed this

Twenty-third Day of December, 2008

JON W. DUDAS
*Director of the United States Patent and Trademark Office*